United States Patent [19]

White

[11] 4,179,812
[45] Dec. 25, 1979

[54] DENTAL BRACKET BONDING AGENT AND METHOD OF USE

[76] Inventor: Velton C. White, 17 N. Broadway, Des Plaines, Ill. 60016

[21] Appl. No.: 830,425

[22] Filed: Sep. 6, 1977

[51] Int. Cl.² .......................... A61C 7/00; B32B 31/00
[52] U.S. Cl. ...................................... 433/9; 156/295; 156/331
[58] Field of Search ............ 32/12, 14 C, 14 A, 14 R, 32/66; 260/42.14, 42.15; 156/276, 295, 331; 401/1, 2

[56] References Cited

U.S. PATENT DOCUMENTS

| | | | |
|---|---|---|---|
| 3,204,828 | 9/1965 | Paulsen | 401/1 |
| 3,250,002 | 5/1966 | Collito | 32/6 |
| 3,895,445 | 7/1975 | Silverman et al. | 32/14 R |
| 4,028,325 | 6/1977 | King et al. | 260/42.15 |
| 4,068,379 | 1/1978 | Miller et al. | 32/14 A |
| 4,072,796 | 2/1978 | Reinhardt et al. | 260/42.15 |

OTHER PUBLICATIONS

R. L. Bowen, "Properties of a Silane-reinforced Polymer for dental Restorations", Jan. 1963 Journal of the Am. Dental Assoc.

Primary Examiner—Russell R. Kinsey
Assistant Examiner—Michael J. Foycik
Attorney, Agent, or Firm—Trexler, Wolters, Bushnell & Fosse, Ltd

[57] ABSTRACT

A bonding material is disclosed for use in securing an orthodontic device, such as an orthodontic bracket, to a tooth. A pre-measured amount of an alphacyanoacrylate resin is provided in a syringe-like collapsible container. A pre-measured amount of an inert, finely divided particulate filler is provided in a bi-layered open-scrim cellulose package. In use, the filler package is placed between the orthodontic device and the tooth, and the resin is applied to the filler and filler package. Heat can be applied to shorten the resin cure time.

9 Claims, 2 Drawing Figures

DENTAL BRACKET BONDING AGENT AND METHOD OF USE

BACKGROUND OF THE INVENTION

This invention relates generally to apparatus for and methods of applying dental brace brackets and other orthodontic appliances to human teeth, and more particularly concerns a substance for and method of directly bonding a dental brace bracket or like orthodontic appliance to teeth.

A relatively common orthodontic procedure for re-aligning human teeth in order to bring them into a desired alignment relies on the use of structures commonly known as braces. In general, orthodontic braces comprise a plurality of brackets, one of which is affixed to each of the teeth whose re-alignment is desired, and one or more force-applying arches or wires attached to the brackets. In use, these stressed arches or wires pull on the brackets in such a way as to urge the teeth into the desired alignment.

According to the modern state of the dental arts, these brackets generally include an arch wire-engaging portion, and a band which is fitted around the individual tooth. These bands can become uncomfortable to the patient, and can act as places where food particles can lodge and become the source of resultant tooth decay.

In view of these shortcomings, it has been provided to affix the dental brace and brackets to a patient's teeth by direct adhesive bonding. One such bonding method is described and claimed in my co-pending U.S. Patent application Ser. No. 760,906 filed Jan. 21, 1977.

Development of a commercially acceptable direct bonding method has been inhibited until recently by a number of problems. Certain candidate substances for the bonding agent have been toxic to an unacceptably high degree. In addition, many bonding agents have provided a bracket-tooth bond which is so weak that the bracket can easily become detached from the tooth. Other proposed bonding agents have provided a tooth-bracket attachment bond which weakens after a period of time, thereby permitting the bracket to break away from the tooth after the dental patient has worn the braces for a comparatively short time. Some bonding agents have permitted the bonded bracket to "creep" or slightly alter its position relative to the tooth, thereby lessening or nullifying the effect of the braces and the orthodontic re-positioning action. Still other bonding agents have provided an effective bond but have proved extremely difficult if not impossible to remove from the tooth once the orthodontic operations have been completed and brace removal has been desired. In some circumstances, these latter bonding agents have been removed only with difficulty or have caused injury to the tooth upon which the bracket was installed.

It is therefore a general object of the present invention to provide a bonding agent, and a method for applying the agent, which will overcome these difficulties.

More specifically, it is an object of the instant invention to provide a bonding agent which is non-toxic to an acceptable degree, which provides a strong bond which will not weaken after prolonged use, which will not permit bracket creep action, and yet which can be dissolved or otherwise altered so as to permit bracket removal when desired.

Another object is to provide such a bonding agent and method for its application which encourage, if not absolutely dictate, proper application. An additional object is to provide a bonding agent and auxiliary substances which are packaged in such a form as to encourage the proper bonding agent preparation application, and use.

Other objects and features of the invention will become more apparent upon reading the following detailed description and upon reference to the drawings. Throughout the drawings, like reference numerals have been used to refer to like parts.

DETAILED DESCRIPITON

Figure 1:
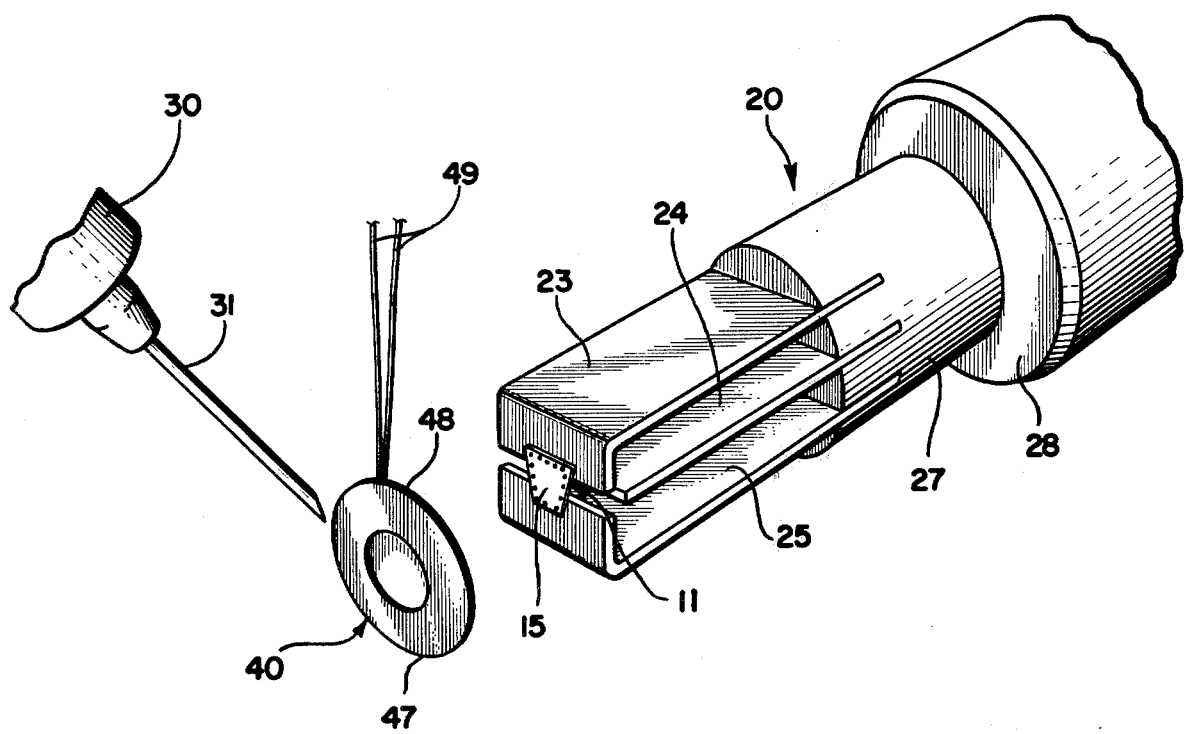
FIG. 1 is a perspective view showing a typical orthodontic device such as a brace bracket as it appears when it is ready for bonding attachment to a tooth, together with bonding substances as they appear when packaged for use with the orthodontic device.
Figure 2:
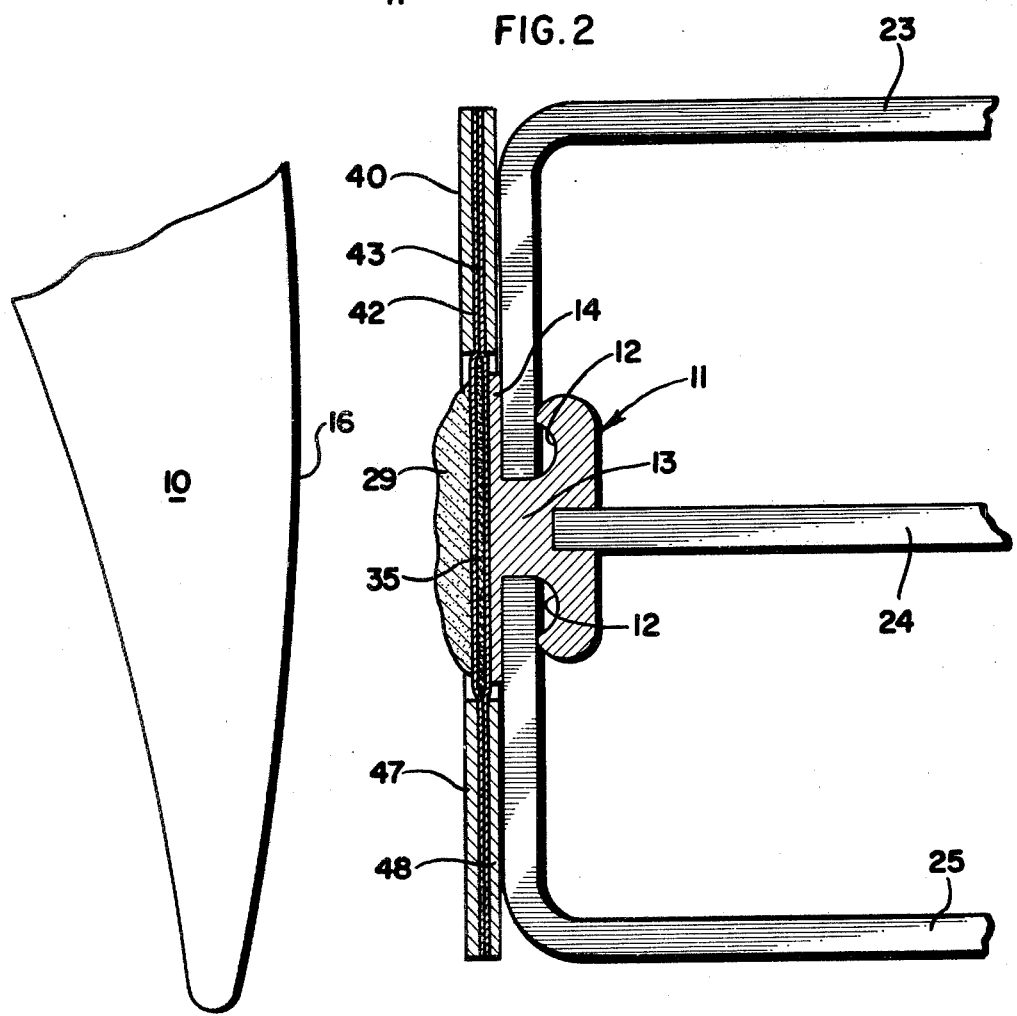
FIG. 2 is a side elevational view of the bonding agent, bonding agent package, orthodontic bracket device, bracket holding structure and a tooth upon which the bracket is to be installed.

While the invention will be described in connection with a preferred embodiment and procedure, it will be understood that it is not intended to limit the invention to this embodiment or procedure. On the contrary, it is intended to cover all alternatives, modifications, and equivalents as may be included within the spirit and scope of the invention as defined by the appended claims.

Turning more specifically to the drawings, there is shown a tooth 10 to which an orthodontic device 11 such as an orthodontic brace bracket is to be directly attached. In general, this bracket 11 includes wire-accepting hook elements 12 emanating from a stem 13 carried upon a bracket base 14. It will be understood that a back side 15 of the base 14 is to be bonded to a front surface 16 of the tooth 10.

A bracket holder 20, which can take the form of a wand or gun or other manipulable shape, is here provided to hold the bracket 11 and to assist in its accurate positioning upon the tooth 10. To this end, bracket-holding blades 23, 24 and 25 extend from a socket 27 which is rotatably carried in a nose portion 28 of the wand holder 20. If desired, this nose portion 28 may include a heater (not shown) to raise the temperature of the blades 23–25 and, consequently, elevate the temperature of the bracket 11 and associated bonding agent constituents. When the temperature is so elevated, bonding agent cure time is shortened, and excess bonding agent is driven from the bonding site. A thermostat can be connected to the heater to prevent the bracket 11 and tooth 10 from being heated to more than a temperature of about 125° F. and so injuring the patient.

When the orthodontist desires to place a bracket such as the orthodontic device 11 against the tooth 10, the bracket 11 is installed upon the holder blades 23, 24 and 25 as shown.

To secure the bracket 11 to the tooth 10, an alphacyanoacrylate bonding constituent 29 is provided. To discourage excessive use of this material, to provide a neat-appearing bond between the bracket 11 and tooth 10, and to encourage accurate placement of the alphacyanoacrylate against the tooth 10, this material can be provided to the orthodontist in a small syringe-like capsule 30 having a hollow, needle-like delivery tube 31. A single drop of the bonding constituent provides a tooth device bond of the desired high strength.

In practice, use of a bead 29 of alphacyanoacrylate resin material alone provides a bond having suitable strength, longevity and low toxicity. However, uncompounded alphacyanoacrylate resin sets or cures so rapidly as to inhibit, if not altogether eliminate, the ability of the orthodontist to accurately place the bracket on the tooth. To overcome this difficulty and in accordance with important features of the present invention, a chemically inert filler material 35, such as finely divided talc, cornstarch, metal silica having a particle size of about 400 microns or the like is incorporated in the alphacyanoacrylate resin material that is applied to the surface of the tooth. It has been found that use of this filler material 35 in connection with the alphacyanoacrylate resin material extends the set time of the mixture suffciently to permit the orthodontist to accurately place the bracket 11 on the tooth 10 while providing a secure, rigid, long-lasting bond between the bracket 11 and the tooth 10.

One eminently useful alphacyanoacrylate resin material for use as the bonding agent of the present invention is the methylcyanoacrylate resin sold by Permabond International Corp. of New York, N.Y., under the name "Permabond No. 130". This is a moderately high viscosity liquid resin which requires only mild heating to produce an acceptable degree of cure.

The methylcyanoacrylate resin material is mixed with the filler material at the time of application and in proportions which optimize the bond strength, preferably in about a 1:1 ratio by weight. In addition, the particle size of the filler material is selected to facilitate its rapid diffusion throughout the mass of resin material in the bead 29, filler material passing a 200-mesh Tyler screen and retained on a 325-mesh Tyler screen having proved useful in this regard. In selection of the filler material, substances which catalyze or otherwise influence the condensation reaction (cure) of the resin are avoided; and such substances as zinc oxide have proved inutile for the purposes of the present invention.

Again, to discourage if not altogether prevent the orthodontist from inadvertently using too much or too little filler material constituent 35 in connection with the bonding agent 29 itself, and in further accordance with the invention, the filler 35 is offered in a previously prepared package 40. This package 40 can take the form of two layers 42 and 43 of non-woven cellulose fiber cloth-like material between which the filler material 35 is carried. It has been found that bond strength is not sufficiently reduced by interposing these two layers 42 and 43 of cellulose scrim between the tooth 10 and bracket 11.

To secure the cellulose layers 42 and 43 together and retain the filler material 35, the layers 42 and 43 can be permanently secured to one another by retaining elements 47 and 48. If desired, these retaining elements 47 and 48 can be inexpensively provided in a form which promotes their easy removal from the finished bracket-tooth bonding site; paper-like gummed reinforcing rings or ring-like elements provide the desired retentive security. String-like members 49 can be offered to further ease manipulation of the package 40. By using the filler package 40 and the resin container 30, the bonding mixture is prepared and mixed in situ, and surprisingly little resin is wasted. Curing action is easily controlled and a neat finished appearance is obtained with ease.

To shorten the bonding agent setting action once the device 11 has been located on its desired position on the tooth 10, the holder 20 heating element is activated and the blades 23, 24 and 25 transmit heat to the bracket device 11, and filler 35 and the bonding agent 29. When bonding agent/filler infusion has been completed and resin curing action is finished and excess bonding agent has been driven off, the holder 20 is removed from the bracket. When all brackets have been bonded in place, the orthodontist wires or arches can be attached.

Removal of the brace bracket 11 is readily accomplished at the option of the orthodontist by flushing the surfaces of the bead 29 with a suitable solvent for the resin material. Nitromethane, dimethylforamide, and methyl ethyl ketone are useful solvents, although nitromethane is preferred because of its low (class III) toxicity and rapid solvating action. After the bracket 11 is removed, the tooth 10 can be given a final wash with the solvent to restore a natural, unmarked appearance.

The invention is claimed as follows:

1. A method of at least temporarily bonding an orthodontic device to a tooth, comprising the steps of: interposing an open-scrim envelope containing a quantity of a finely divided, inert, particulate filler material between the device and the tooth; infusing an alphacyanoacrylate resin throughout said filler material whereby the curing time of said resin is increased; pressing the device toward the tooth to compress the matrix of filler material and resin between said device and said tooth; and retaining said device and matrix in place until said resin has cured.

2. A method according to claim 1 which further includes heating the resin to shorten the cure time.

3. A method according to claim 1 which further includes applying a solvent to the matrix of resin and filler material after the resin has cured in order to weaken the resin bond and permit removal of the orthodontic device and the matrix from the tooth.

4. A bonding arrangement for securing an orthodontic device to a tooth, said arrangement comprising: and envelope having a first edged layer of open-scrim cellulose material adjacent the tooth, a second edged layer of open-scrim cellulose material adjacent the device, and affixed at said edge to the first layer edge, and finely divided, inert, particulate filler material interjacent said first layer and said second layer; said envelope being infused with an alphacyanoacrylate resin to form a matrix of filler material and resin, said matrix being infused, in turn, through said first and said second envelope layers to extend directly from the tooth to the orthodontic device, whereby the curing time of said resin is sufficiently retarded to allow the proper positioning of said device.

5. A bonding arrangement according to claim 4 wherein said resin is methylcyanoacrylate.

6. A bonding arrangement according to claim 4 wherein said filler material is talc.

7. A bonding arrangement according to claim 4 wherein said filler material is cornstarch.

8. A bonding arrangement according to claim 4 wherein said resin and said filler material are mixed in about 1:1 proportion by weight.

9. A bonding arrangement according to claim 4 wherein said filler material is a metal silica having a particle size of substantially 400 microns.

* * * * *